United States Patent
Czollner et al.

(10) Patent No.: US 7,385,060 B2
(45) Date of Patent: Jun. 10, 2008

(54) METHOD FOR PRODUCING SALTS OF TOLPERISONE

(75) Inventors: Laszlo Czollner, Ebenfurth (AT); Beate Kälz, Steinbrunn (AT); Jan Rothenburger, Oslip (AT); Stefan Welzig, Vienna (AT)

(73) Assignee: Sanochemia Pharmazeutika AG, Wien (AT)

( * ) Notice: Subject to any disclaimer, the term of this patent is extended or adjusted under 35 U.S.C. 154(b) by 525 days.

(21) Appl. No.: 10/537,434

(22) PCT Filed: Mar. 31, 2003

(86) PCT No.: PCT/AT03/00092

§ 371 (c)(1),
(2), (4) Date: Jul. 15, 2005

(87) PCT Pub. No.: WO2004/050648

PCT Pub. Date: Jun. 17, 2004

(65) Prior Publication Data

US 2006/0041141 A1 Feb. 23, 2006

(30) Foreign Application Priority Data

Dec. 5, 2002 (AT) .............................. A 1823/2002

(51) Int. Cl.
*C07D 211/06* (2006.01)

(52) U.S. Cl. ...................... 546/237; 546/184; 546/192; 546/236

(58) Field of Classification Search ................ 546/184, 546/192, 236, 237
See application file for complete search history.

(56) References Cited

FOREIGN PATENT DOCUMENTS

JP 52095674 8/1977

OTHER PUBLICATIONS

Sumita et al., "A Modified Mannich Reaction Using 1,3-Dioxolane," *Chemical and Pharmaceutical Bulletin*, Pharmaceutical Society of Japan, Tokyo, JP, 42(8):1676-1678 (Aug. 1, 1994).
Yokoyama et al., "4'-Substituted-2-methyl-3-piperidinopropiophenones," retrieved from STN Database accession No. 88:22646, XP002252004 abstract-& JP 52 095674 A (Nippon Carbide Industries Co., Inc., Japan) (Aug. 11, 1977).
Sumita et al., "A Modified Mannich Reaction Using 1,3-Dioxolane," *Chemical and Pharmaceutical Bulletin*, Pharmaceutical Society of Japan, Tokyo, JP, 42(8):1676-1678 (Aug. 1, 1994).
Yokoyama et al., "4'-Substituted-2-methyl-3-piperidinopropiophenones," retrieved from STN Database accession No. 88:22646, XP002252004 abstract-& JP 52 095674 A (Nippon Carbide Industries Co., Inc., Japan) (Aug. 11, 1977) (1 page).

*Primary Examiner*—Golam M. M. Shameem
(74) *Attorney, Agent, or Firm*—Robins & Pasternak LLP

(57) ABSTRACT

The invention relates to a method for producing an addition salt of 2,4'-dimethyl-3-piperidino-propiophenone (tolperisone) with a pharmaceutically acceptable acid, of formula (I). According to the invention, 4-methylpropiophenone is reacted with piperidine hydrochloride and 1,2-dioxalane in the presence of an acid serving as a catalyst, and the tolperisone obtained in the form of an acid addition salt is separated by filtering after the reaction mixture has cooled down (I)

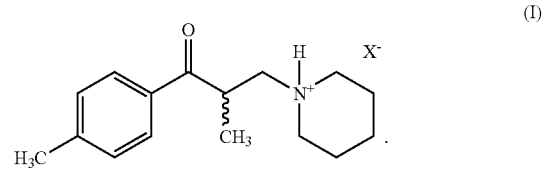

6 Claims, No Drawings

METHOD FOR PRODUCING SALTS OF TOLPERISONE

The invention relates to a method for manufacturing organic and inorganic acid addition salts and hydrates of tolperisone having the general formula B:

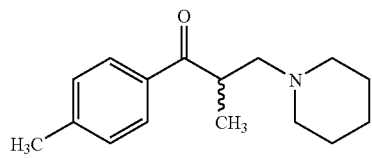

(B)

Tolperisone is the international name for a muscle relaxant having the chemical name (RS)-2,4'-Dimethyl-3-piperidinopropiophenone and also having the molecular formula $C_{16}H_{23}NO$. Tolperisone is a muscle-relaxing pharmaceutical, with the following formula A (A)

The main indications for tolperisone are illnesses which are accompanied by painful muscle spams, e.g. spinal column syndromes, muscular pain with degenerative illnesses, sports and occupational repetitive motion syndromes and the Fibromyalgia syndrome.

An advantage of the treatment with tolperisone is the fact that functional parameters e.g. the mobility of the patient, is also improved. Patients having long-term administration of tolperisone have a good therapeutic relationship and the confidence basis necessary for therapeutic success by the absence of central side effects usually associated with the further employment of this medicine.

Tolperisone and its salts with the general formulas A and B are well-known and can be manufactured by different chemical pathways. The well-known methods in the synthetic art have the disadvantage that they utilize raw materials that are not commercially available, and also have the drawbacks of complicated reaction conditions on an industrial scale which lead to low yields.

J. Labelled Cpd. Radiopharm 42, 1125-1134 (1999)

In order to be able to manufacture radioactively labeled tolperisone, Ditriech provides a direct synthesis pathway on the basis of 4'-methylacetophenone and paraformaldehyde. The multi-level synthesis leads to a mixture of substances and the tolperisone can only be isolated by column chromatography.

Jap. Pat. 04005283 A2 19920109

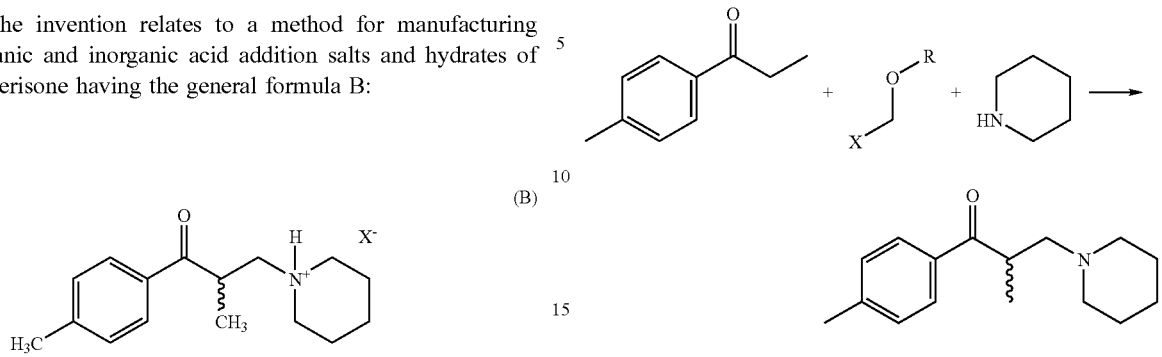

Disadvantages of this method are the multi-level synthesis, the intermediate product must be isolated and purified.

Jap. Pat. 54032480 19790309

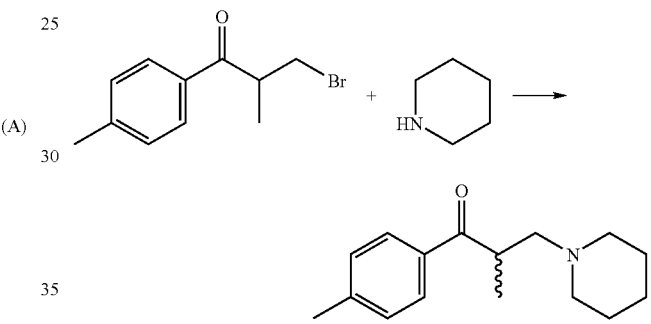

The production of the halogen derivative is complex and expensive.

Jap. Pat. 54036274 19790316

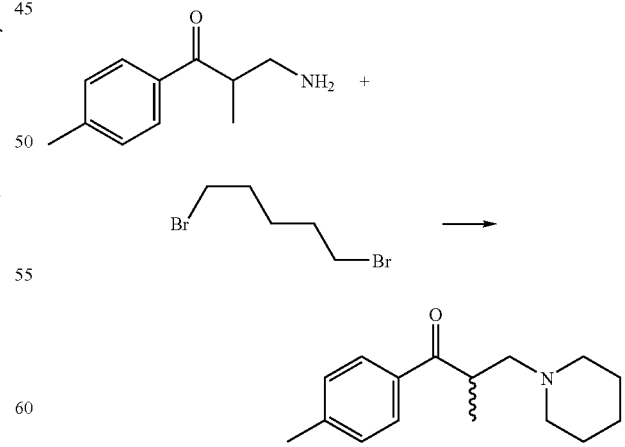

This synthesis pathway starts from expensive raw materials and it develops several by-products (ie., dibromopentane).

Jap. Pat. 54030178 19790306

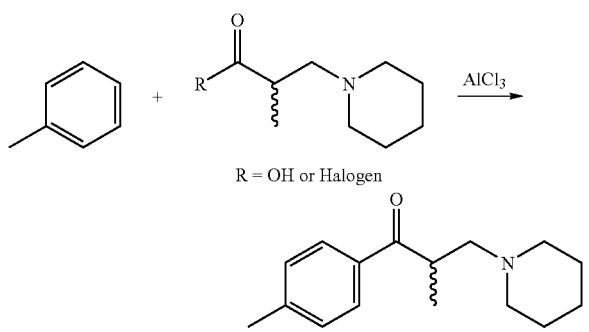

The raw material needed for this synthetic pathway must be manufactured over several stages. Furthermore, the reaction must be worked under exclusion of humidity to avoid the hydrolysis of aluminum trichloride.

Jap. Pat. 54027571 19790301

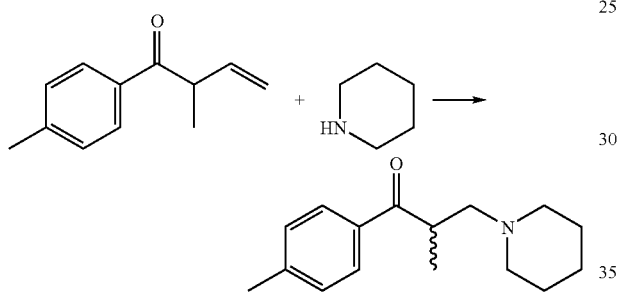

This synthesis pathway starts from expensive raw materials and it develops several by-products (e.g. vinyl compounds).

Chem. Pharm. Bull. 42, 1676 (1994):

Kazuharu et al. describe in Chem. Pharm. Bulletin 42(8) 1676 (1994) the production of tolperisone by the Mannich reaction. The published yields are relatively high, however several by-products are removed by aqueous extraction. The multi-level processing is unfavorable and expensive, since the substance is isolated first in oily form and only afterwards as the hydrochloride.

RO 75-83082 19750804 (CAN 98: 125629)

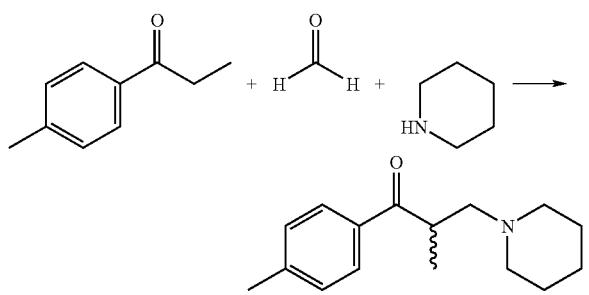

The use of formaldehyde that is not in protected form has several disadvantages, like water in the reaction mixture, high toxicity (IHL-TCLO HMN 17 mg/m$^3$/30 m; ORL-RAT LD$_{50}$ 100 mg kg$^{-1}$) or formation of very difficultly soluble paraformaldehyde.

Jap. Pat. 20,390 (1965)

Matatsugu et al. published a method for the production of tolperisone on the basis of paraformaldehyde in a mixture of nitromethane:ethanol:toluene (40:5,5:11) using aqueous hydrochloric acid. The indicated reaction results in a conglomerate and working with nitromethane is expensive due to its danger.

Hung. Pat. 144,997 (1956)

Nádor et al. describes an industrial method for the production of tolperisone using ethanol saturated with gaseous formaldehyde. This method leads to tolperisone hydrochloride, the yields however are low and working with gaseous formaldehyde is expensive due to its danger.

Among the unwanted isomers which are notable in particular are:

(C): 2-Methyl-1-(3-methylphenyl)-3-piperidin-1-ylpropan-1-one;
(D): 2-Methyl-1-(2-methylphenyl)-3-piperidin-1-ylpropan-1-one;

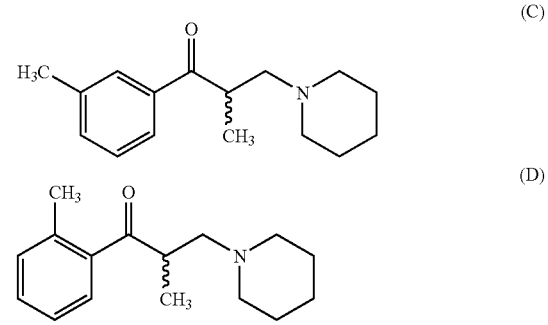

On the basis of the synthesis method and the quality (purity) of the assigned basic materials the following impurities in the final product (tolperisone) are possible:

| Component | Chemical name | Chemical Structure |
|---|---|---|
| Piperidine HCl | Piperidine hydrochloride | 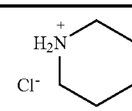 |
| C | 2-methyl-1-(3-methylphenyl)-3-(1-piperidinyl)-propanone hydrochloride 3-tolperisone hydrochloride | 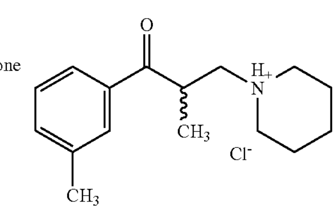 |
| 4-MMP | 1-(4-methylphenyl)-propanone 4-methylpropiophenone | 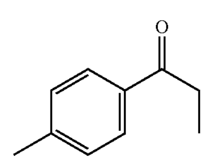 |

-continued

| Component | Chemical name | Chemical Structure |
|---|---|---|
| E | 2-methyl-1-(4-methylphenyl)-propenone | 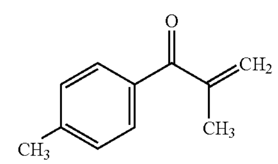 |
| D | 2-methyl-1-(2-methylphenyl)-3-(1-piperidinyl)-propanone hydrochloride 2-tolperisone hydrochloride | 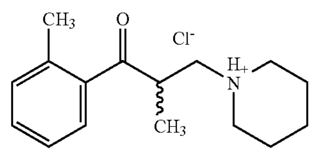 |

The objective of the invention is to develop an improved method for manufacturing tolperisone with improved purity and its salts, feasible in a technical scale, without the disadvantages that arise from the well-known synthetic pathways.

The objective is accomplished with a method, which exhibits the characteristics of patent claim 1.

Favourable synthetic arrangements according to the methods of the invention are the subject of the claims.

With the below described analytical methods these impurities can be ascertained to be near 0.1%.

The analysis methods are described below.

1.1. Method 1: Analysis of the Content of Tolperisone and Impurities 3-tolperisone (C), 4 Methylpropiophenone (4-mpp) and Vinylketone (E):

The determination of the content of tolperisone and the impurities mentioned above takes place by means of measurements against external standards on a HPLC system with UV detection. The stationary phase consists of a functionalized polysaccharide. As mobile phase a binary system of a borate buffer and an organic modifier (acetonitrile) is used.

1.2. Method 2: Analysis of the Content 2-tolperisone (D):

For the determination of the content of 2-tolperisone a HPLC system along with UV detection is likewise used. The stationary phase is a calixarene bound on silicate. As mobile phase a mixture of phosphate buffer and methanol is used.

1.3. Method 3: Analysis of the content of Piperidine Hydrochloride:

For the regulation of piperidine HCl a quantitative LC/MS method is used. The stationary phase consists of octadecysilyl derivatized silica gel. The binary mobile phase contains tri-chloro acetic acid and methanol.

With the described methods also the levels of C and D can be ascertained (determined), although these position isomers hardly differ in their chemical characteristics from tolperisone and therefore are separated with difficulty.

So far for determining the content of tolperisone a regular titrimetric method was used (Pharm. Jap. XI), with which only the sum of the levels B, C and D can be determined.

With the new HPLC method for determining tolperisone, 2-tolperisone, 3-tolperisone and the remaining impurities and the LC/MS method for determining piperidine hydrochloride, the problems of the well-known analyses are eliminated.

With these analysis methods, the purity was determined according to the invention for the tolperisone made according to the invention and for tolperisone preparations available in the marketplace.

The results are summarized in the following table:

| Product description | 2-Tolperisone | 3-Tolperisone | Piperidine | Vinyl Ketone | 4-MPP |
|---|---|---|---|---|---|
| Mydeton 50 mg Tablets from Gedeon Richter | 0.3% | 0.8% | <0.05% | <0.05% | <0.05% |
| Mydeton 510 mg Tablets from Gedeon Richter | 0.6% | 1.2% | <0.05% | <0.05% | <0.05% |
| Mydocalm 50 mg Tablets From Strathmann | 0.6% | 1.1% | <0.05% | <0.05% | <0.05% |
| Toperisone of the present invention | <0.05% | 0.1% | <0.05% | <0.05% | <0.05% |

The analyses summarized in the table show the fact that tolperisone is clearly worse in products present in the market in its purity profile, particularly in the content of position isomers, than the tolperisone available in accordance with the invention and thus does not correspond to the current guidelines of the European regulatory agencies.

The method according to invention for the synthesis of tolperisone can be shown as follows:

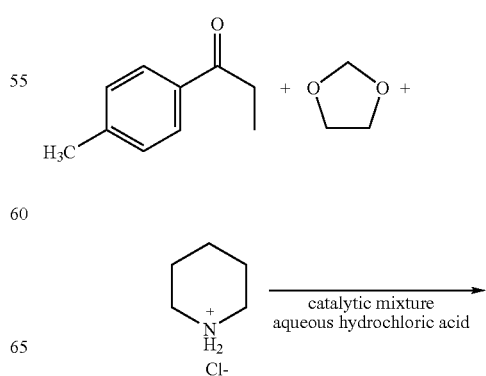

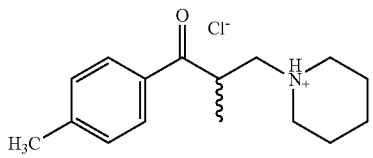

As the starting materials 4-methylpropiophenone, piperidine hydrochloride and 1,2-dioxolane are used as reaction partners and the latter is used preferentially also as solvent.

Using 1,2-dioxolane in place of formaldehyde and the high yield achieved after the direct isolation of tolperisone makes the single-step reaction economical also on an industrial scale.

With the method according to the invention it is feasible that the starting 4-methylpropiophenone may be contaminated with up to 5% 3-methylpropiophenone and up to 2% 2-methylpropiophenone, and with the methods according to the invention nevertheless the necessary final product purity is attained.

With the method according to the invention for manufacturing salts of tolperisone of the formula B aqueous hydrochloric acid can be used in catalytic quantities for the aminomethylation reaction accomplished in 1,2-dioxolane. Thus the final product of the salts of tolperisone can be separated easily by the addition of ethyl acetate and tert-butyl methylether in accordance with general formula B for example as chloride (X=Cl) and can be separated from the reaction mixture by precipitation.

The separated salt of tolperisone possesses already high purity and a favorable impurity profile, however if necessary it can be further purified e.g. by further recrystallization.

Altogether the method of the invention is suitable also for carrying out on an industrial scale, since a purification step represents a small expenditure by means of salt precipitation only. The method of the invention can be implemented and also automated.

The method of the invention permits manufacturing of suitable salts of tolperisone with acids by addition of the pharmaceutical active, to preferential acids such as mineral acids, and more in particular hydrochloric acid.

Favourable method and variants thereof according to the invention are described on the basis the following examples:

EXAMPLE 1

Production of Tolperisone Hydrochloride

In a 3-L-three neck flask with a reflux condenser, a calcium chloride drying tower, and under an argon flow, 200 ml of 1,3-dioxolane and 146.2 ml of 4-methylpropiophenone are subjected to agitation and then there is added through a funnel 100 g piperidine hydrochloride and 4.0 ml of 33% aqueous hydrochloric acid. The powder in the funnel is washed afterwards with 20 ml 1,3-dioxolane, and the stirrer is switched on in the reaction flask. The reaction mixture is purged once with argon and stirred at 100-105° C. bath temperature (83-86° C. interior temperature). The white precipitate dissolves after approximately 15-16 hours. After 18-20 hours the thin layer chromatogram shows no more piperidine. After 24 hours the heating is switched off and the oil bath is removed and while still warm, and under vigorous stirring to the clear reaction solution, there is added 800 ml ethyl acetate and then the solution is cooled to ambient temperature and then further treated with 400 ml methyl tert-butylether (MTBE). The resulting precipitate is agitated at α to 10° C. for an additional 2 hours, and then filtered off over a glass filter (Po-3) and washed afterwards twice with 200 ml MTBE each time. The substance is dried in the vacuum drying oven at 75-80° C. and 20-40 mbar for 16 to 24 hours.

Yield: 206.5 g (89.1%, computed on piperidine hydrochloride) colorless powder
mp.: 169° C.
Analysis:

| Melting point | 2-Tolperisone | 3-Tolperisone | 4-Tolperisone | Piperidine | Other Impurities | 4-MPP |
|---|---|---|---|---|---|---|
| 169° C. | 0.22% | 0.30% | 98.0% | <0.05% | <0.05% | <0.05% |

EXAMPLE 2

Purification of Tolperisone Hydrochloride

Into a 500 ml-three-necked flask with stirrer, reflux condenser and dropping funnel 58.0 g tolperisone are added and mixed with 87 ml of isopropyl alcohol. The reaction mixture is heated up to the boiling point, whereby a clear solution develops. The warm reaction solution is mixed with 261 ml MTBE and cooled under constant stirring to ambient temperature. The resulting suspension is cooled under stirring conditions at ambient temperature for 14-18 hours, then further cooled to 5-10° C. and after 2-3 hours of stirring it is filtered off. The precipitate is washed afterwards twice with 80 ml MTBE each and dried in the vacuum oven at 55-60° C. and 30-50 mbar for 14 to 24 hours.

Yield: 48.0 g (82.9%) colorless substance
Smp.: 171° C.
analysis:

| Melting point | 2-Tolperisone | 3-Tolperisone | 4-Tolperisone | Piperidine | Other Impurities | 4-MPP |
|---|---|---|---|---|---|---|
| 171° C. | <0.05% | 0.16% | 98.9% | <0.05% | <0.05% | <0.05% |

EXAMPLE 3

Industrial Production of Tolperisone Hydrochloride 75 kg piperidine hydrochloride and 105 kg 4-methylpropiophenone are heated to 90° C. with 180 kg of 1,3-dioxolane and 12 kg of hydrochloric acid under a nitrogen atmosphere for 7 to 20 hours. With addition of 500 kg of ethyl acetate and 440 kg MTBE at a temperature in the range of (40-80° C.), a suspension of the product is produced. After that the solid is separated from the liquid as a damp product and then dried at 60-80° C. in the vacuum oven (200-500 mbar) over a period of 12-24 hours whereby 140 kg (81.5%) of colorless crystals are isolated.
MP: 170° C.
Analysis:

| Melting point | 2-Tolperisone | 3-Tolperisone | 4-Tolperisone | Piperidine | Other Impurities | 4-MPP |
|---|---|---|---|---|---|---|
| 170° C. | 0.47% | 0.36% | 97.8% | <0.9% | <0.05% | <0.05% |

EXAMPLE 4

Industrial Recrystallization of Tolperisone Hydrochloride 60 kg of tolperisone (from example 3) are heated up in 410 kg of 2-Butanone and 71 kg of isopropanol under nitrogen atmosphere and under reflux. After an optional hot filtration, by cooling a suspension of the product results. After that the solid is separated from the liquid as a damp product and then dried at 60-80° C. in the vacuum oven (200-500 mbar) over a period of 12-24 hours whereby 45 kg (75%) of colorless crystals are isolated.
mp.: 173° C.
Analysis:

| Melting point | 2-Tolperisone | 3-Tolperisone | 4-Tolperisone | Piperidine | Other Impurities | 4-MPP |
|---|---|---|---|---|---|---|
| 173° C. | <0.05% | 0.14% | 98.5% | <0.05% | <0.05% | <0.05% |

EXAMPLE 5

Industrial Production of Tolperisone Hydrochloride 107 kg of piperidine hydrochloride and 150 kg of 4-methylpropionphenone are heated up to 90° C. with 159 kg of 1,3-dioxolane and 107 L of hydrochloric acid under a nitrogen atmosphere for 7 to 20 hours. With addition of 783 kg ethyl acetate and 322 kg of methyl tert-butylether at a temperature of (40-80° C.), a suspension of the product is produced. After separating the liquid, the damp product is dried at 60-80° C. in the vacuum oven (200-500 mbar) for a period of 12-24 hours, whereby 200 kg (81,5%) colorless crystals are isolated.
mp.: 170° C.

EXAMPLE 6

Industrial Recrystallization of Tolperisone Hydrochloride 190 kg of tolperisone (from example 5) in 1300 kg of 2-butanone and 224 kg isopropanol are heated under nitrogen atmosphere and refluxed. After an optimal hot filtration, by cooling a suspension of the product is produced. After separating the liquid, the damp product is dried at 60-80° C. in the vacuum oven (200-500 mbar) for a period of 12-24 hours, whereby 143 kg (75%) colorless crystals are isolated.
mp.: 173° C.

In Summary, An Example of the Invention can be Represented as Follows:

A method is described for manufacturing an acid addition salt of 2,4'-dimethyl-3-piperidinopropiophenone (tolperisone) with a pharmaceutical acceptable acid, of the formula

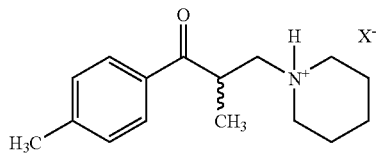

by reacting 4-methylpropiophenone with piperidine hydrochloride and 1,2-dioxolane in the presence of an acid as catalyst and the resulting tolperisone as an acid addition salt is filtered off after cooling of the reaction mixture.

The invention claimed is:

1. A method for manufacturing pharmaceutically acceptable acid addition salts of 2,4'-dimethyl-3-piperidinopropiophenone (tolperisone), of formula (A)

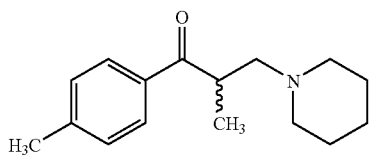
(A)

said acid addition salts having a formula (B)

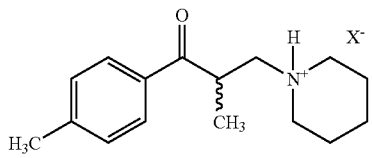
(B)

comprising reacting 4-methylpropiophenone of the formula

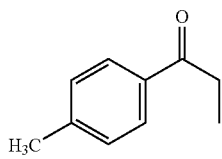

with piperidine hydrochloride of the formula

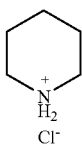

and 1,2-dioxolane of the formula

in the presence of a catalytic amount of an acid, wherein tolperisone is separated as an acid addition salt in accordance with the general formula (B) after cooling the reaction mixture by addition of ethyl acetate and tert-butylmethylether to cause precipitation.

2. A method according to claim 1, wherein the acid is an inorganic acid.

3. A method according to claim 1, wherein the acid is aqueous hydrochloric acid.

4. A method according to claim 1, wherein the reaction is carried out in a solvent.

5. A method according to claim 4, wherein the reaction is accomplished in 1,2-dioxolane as a solvent in a concentration range from 1 to 6 mol/lit.

6. A method according to claim 5, wherein the reaction is accomplished in 1,2-dioxolane as a solvent at a concentration of 3.6 mol/lit.

* * * * *